United States Patent
Oda et al.

(10) Patent No.: US 9,963,584 B2
(45) Date of Patent: May 8, 2018

(54) BLOCK COPOLYMER COMPOSITION, PRODUCTION METHOD THEREFOR, AND FILM

(71) Applicant: ZEON CORPORATION, Chiyoda-ku, Tokyo (JP)

(72) Inventors: Ryoji Oda, Tokyo (JP); Yuta Ishii, Tokyo (JP)

(73) Assignee: ZEON CORPORATION, Chiyoda-ku, Tokyo (JP)

( * ) Notice: Subject to any disclaimer, the term of this patent is extended or adjusted under 35 U.S.C. 154(b) by 36 days.

(21) Appl. No.: 15/107,179

(22) PCT Filed: Dec. 26, 2014

(86) PCT No.: PCT/JP2014/084665
§ 371 (c)(1),
(2) Date: Jun. 22, 2016

(87) PCT Pub. No.: WO2015/099163
PCT Pub. Date: Jul. 2, 2015

(65) Prior Publication Data
US 2017/0009070 A1    Jan. 12, 2017
US 2017/0369699 A9    Dec. 28, 2017

(30) Foreign Application Priority Data
Dec. 27, 2013 (JP) ................................ 2013-270890

(51) Int. Cl.
*C08L 53/02*    (2006.01)
*C08J 5/18*    (2006.01)

(52) U.S. Cl.
CPC ............... *C08L 53/02* (2013.01); *C08J 5/18* (2013.01); *C08J 2353/02* (2013.01); *C08L 2203/16* (2013.01); *C08L 2205/025* (2013.01)

(58) Field of Classification Search
CPC ............................ C08L 53/02; C08L 2205/025
See application file for complete search history.

(56) References Cited

U.S. PATENT DOCUMENTS

| 4,107,354 A * | 8/1978 | Wilkenloh ......... H01B 11/1839 156/51 |
| 2004/0102576 A1 | 5/2004 | Matsui et al. |
| 2005/0009990 A1 * | 1/2005 | Knoll ................. C08F 297/04 525/89 |
| 2005/0089702 A1 | 4/2005 | Matsui et al. |
| 2006/0211823 A1 * | 9/2006 | Kurimura ............ C08F 297/04 525/242 |
| 2011/0046307 A1 | 2/2011 | Takeshi et al. |

FOREIGN PATENT DOCUMENTS

| JP | 2006-089593 A | 4/2006 |
| JP | 2008-274299 A | 11/2008 |
| JP | 2010-202716 A | 9/2010 |
| JP | 2011-143615 A | 7/2011 |
| JP | 2013-139514 A | 7/2013 |
| JP | 5555329 B2 | 7/2014 |
| WO | 2009/123089 A1 | 10/2009 |
| WO | 2012/063812 A1 | 5/2012 |

OTHER PUBLICATIONS

Mar. 24, 2015, International Search Report issued in the International Patent Application No. PCT/JP2014/084665.
Jun. 28, 2016, International Preliminary Report on Patentability issued in the International Patent Application No. PCT/JP2014/084665.

* cited by examiner

*Primary Examiner* — Jeffrey C Mullis
(74) *Attorney, Agent, or Firm* — Kenja IP Law PC

(57) ABSTRACT

The present invention provides a block copolymer composition comprising a block copolymer A represented by formula (A) and a block copolymer B represented by formula (B), the block copolymer composition having a water content of 200 ppm by weight or less when the block copolymer composition has been formed in a shape of pellets, dried, and allowed to stand at a temperature of 37° C. and a relative humidity of 70% for 24 hours. In the formulas, $Ar1^a$, $Ar1^b$, and $Ar2^b$ are aromatic vinyl polymer blocks having a weight average molecular weight of 6,000-18,000, $Ar2^a$ is an aromatic vinyl polymer block having a weight average molecular weight of 40,000-400,000, and $D^a$ and $D^b$ are specific conjugated diene polymer blocks. The block copolymer composition has a high modulus of elasticity, exhibits low tension set, and ensures that the formation of a hole is prevented when a film is formed by melt-forming the block copolymer composition.

$Ar1^a$-$D^a$-$Ar2^a$    (A)

$Ar1^b$-$D^b$-$Ar2^b$    (B)

1 Claim, No Drawings

BLOCK COPOLYMER COMPOSITION, PRODUCTION METHOD THEREFOR, AND FILM

TECHNICAL FIELD

The present invention relates to a block copolymer composition that has a high modulus of elasticity, exhibits low tension set, and ensures that the formation of a hole is prevented when a film is formed by melt-forming the block copolymer composition, a method for producing the block copolymer composition, and a film obtained by melt-forming the block copolymer composition.

BACKGROUND ART

An aromatic vinyl-conjugated diene-aromatic vinyl block copolymer (i.e., thermoplastic elastomer) exhibits excellent elasticity and flexibility, and is used as a material for producing an elastic film that is used when producing a sanitary article (e.g., disposable diaper and sanitary item), for example.

A sanitary article (e.g., disposable diaper and sanitary item) is required to follow the motion of the wearer, and fit the wearer, and an elastic film is used to form various parts of the sanitary article. For example, an elastic film is provided around the thigh opening, around the waist opening, on the side part, and the like when producing a pull-up diaper (i.e., disposable diaper). Since it is necessary to prevent the displacement of the sanitary article even when the wearer makes a large motion, or wears the sanitary article for a long time, an elastic film used for such an application is required to have a high modulus of elasticity and exhibit low tension set.

Patent Literature 1 and 2 disclose a block copolymer composition that includes an asymmetric aromatic vinyl-conjugated diene-aromatic vinyl block copolymer in which the aromatic vinyl polymer blocks differ in weight average molecular weight (weight average molecular weight range), and an aromatic vinyl-conjugated diene-aromatic vinyl block copolymer having a specific configuration that differs from the configuration of the asymmetric aromatic vinyl-conjugated diene-aromatic vinyl block copolymer, as a material formed of an aromatic vinyl-conjugated diene-aromatic vinyl block copolymer that can meet the above demand. The block copolymer compositions disclosed in Patent Literature 1 and 2 have a high modulus of elasticity, exhibit low tension set, and exhibit mechanical properties suitable for a material for forming an elastic film used for a sanitary article.

However, the formation of a hole may occur when a film is formed by melt-forming the block copolymer composition specifically disclosed in Patent Literature 1 or 2. When a hole is formed in an elastic film used for a sanitary article, the mechanical properties of the film are impaired, and breakage of the film may occur, for example. Therefore, it is strongly desired to prevent the formation of a hole.

CITATION LIST

Patent Literature

Patent Literature 1: WO2009/123089 (US2011046307A)
Patent Literature 2: JP-A-2010-202716

SUMMARY OF INVENTION

Technical Problem

The invention was conceived in view of the above situation. An object of the invention is to provide a block copolymer composition that has a high modulus of elasticity, exhibits low tension set, and ensures that the formation of a hole is prevented when a film is formed by melt-forming the block copolymer composition, a method for producing the block copolymer composition, and a film obtained by melt-forming the block copolymer composition.

Solution to Problem

The inventors of the invention conducted extensive studies in order to achieve the above object. As a result, the inventors found that the block copolymer composition specifically disclosed in Patent Literature 1 includes water that is considered to be derived from water in air, and the formation of a hole occurs due to the water included in the block copolymer composition when a film is formed by melt-forming the block copolymer composition. The inventors conducted further studies, and found that, when a block copolymer composition that includes two types of block copolymers that differ in structure (i.e., two types of block copolymers that respectively have specific structures) (see Patent Literature 1) is produced to exhibit such a low hygroscopicity that the block copolymer composition rarely absorbs water (moisture) in air, it is possible to prevent the formation of a hole when a film is formed by melt-forming the block copolymer composition. This finding has led to the completion of the invention.

According to a first aspect of the invention, a block copolymer composition includes a block copolymer A represented by the following formula (A) and a block copolymer B represented by the following formula (B), the weight ratio (AB) of the block copolymer A to the block copolymer B in the block copolymer composition being 36/64 to 85/15, the ratio of an aromatic vinyl monomer unit with respect to the total polymer component included in the block copolymer composition being 27 to 70 wt %, and the block copolymer composition having a water content of 200 ppm by weight or less when the block copolymer composition has been formed in the shape of pellets, dried, and allowed to stand at a temperature of 37° C. and a relative humidity of 70% for 24 hours, $$Ar1^a\text{-}D^a\text{-}Ar2^a \quad (A)$$

$$Ar1^b\text{-}D^b\text{-}Ar2^b \quad (B)$$

wherein each of $Ar1^a$, $Ar1^b$, and $Ar2^b$ is independently an aromatic vinyl polymer block having a weight average molecular weight of 6,000 to 18,000, $Ar2^a$ is an aromatic vinyl polymer block having a weight average molecular weight of 40,000 to 400,000, and each of $D^a$ and $D^b$ is independently a conjugated diene polymer block having a vinyl bond content of 1 to 20 mol % and a weight average molecular weight of 40,000 to 400,000.

According to a second aspect of the invention, a method for producing the block copolymer composition includes:
a step (1) that polymerizes an aromatic vinyl monomer in a solvent using a polymerization initiator to obtain a solution including an aromatic vinyl polymer having an active terminal;
a step (2) that adds a conjugated diene monomer to the solution including the aromatic vinyl polymer having an active terminal that has been obtained by the step (1), and polymerizes the conjugated diene monomer to obtain a solution including an aromatic vinyl-conjugated diene block copolymer having an active terminal;

a step (3) that adds an aromatic vinyl monomer to the solution including the aromatic vinyl-conjugated diene block copolymer having an active terminal that has been obtained by the step (2), and polymerizes the aromatic vinyl monomer to obtain a solution including an aromatic vinyl-conjugated diene-aromatic vinyl block copolymer having an active terminal;

a step (4) that adds a polymerization terminator to the solution including the aromatic vinyl-conjugated diene-aromatic vinyl block copolymer having an active terminal that has been obtained by the step (3) in a ratio of less than 1 molar equivalent with respect to the active terminal to partly inactivate the active terminal of the aromatic vinyl-conjugated diene-aromatic vinyl block copolymer to obtain a solution including the block copolymer B;

a step (5) that adds an aromatic vinyl monomer to the solution including the block copolymer B that has been obtained by the step (4), and polymerizes the aromatic vinyl monomer to obtain a solution including the block copolymer B and the block copolymer A; and a step (6) that collects the block copolymer composition from the solution including the block copolymer B and the block copolymer A that has been obtained by the step (5).

According to a third aspect of the invention, a film is obtained by melt-forming the block copolymer composition.

Advantageous Effects of Invention

The aspects of the invention thus provide a block copolymer composition that has a high modulus of elasticity, exhibits low tension set, and ensures that the formation of a hole is prevented when a film is formed by melt-forming the block copolymer composition, a method for producing the block copolymer composition, and a film obtained by melt-forming the block copolymer composition.

DESCRIPTION OF EMBODIMENTS

The exemplary embodiments of the invention are described in detail below.
1) Block Copolymer Composition According to one embodiment of the invention, a block copolymer composition includes a block copolymer A represented by the following formula (A) and a block copolymer B represented by the following formula (B), the weight ratio (AB) of the block copolymer A to the block copolymer B in the block copolymer composition being 36/64 to 85/15, the ratio of an aromatic vinyl monomer unit with respect to the total polymer component included in the block copolymer composition being 27 to 70 wt %, and the block copolymer composition having a water content of 200 ppm by weight or less when the block copolymer composition has been formed in the shape of pellets, dried, and allowed to stand at a temperature of 37° C. and a relative humidity of 70% for 24 hours.

  (A)

  (B)

In the formula (A), $Ar1^a$ is an aromatic vinyl polymer block having a weight average molecular weight of 6,000 to 18,000, $Ar2^a$ is an aromatic vinyl polymer block having a weight average molecular weight of 40,000 to 400,000, and $D^a$ is a conjugated diene polymer block having a vinyl bond content of 1 to 20 mol % and a weight average molecular weight of 40,000 to 400,000.

In the formula (B), each of $Ar1^b$ and $Ar2^b$ is independently an aromatic vinyl polymer block having a weight average molecular weight of 6,000 to 18,000, and $D^b$ is a conjugated diene polymer block having a vinyl bond content of 1 to 20 mol % and a weight average molecular weight of 40,000 to 400,000.

Each aromatic vinyl polymer block ($Ar1^a$, $Ar2^a$, $Ar1^b$, and $Ar2^b$) included in the block copolymer A and the block copolymer B is a polymer block that includes an aromatic vinyl monomer unit.

An aromatic vinyl monomer that is used to produce the aromatic vinyl monomer unit is not particularly limited as long as the aromatic vinyl monomer is an aromatic vinyl compound. Examples of the aromatic vinyl monomer include styrene; a styrene derivative that is substituted with an alkyl group, such as α-methylstyrene, 2-methyl styrene, 3-methyl styrene, 4-methyl styrene, 2-ethyl styrene, 3-ethyl styrene, 4-ethyl styrene, 2,4-diisopropylstyrene, 2,4-dimethyl styrene, 4-t-butyl styrene, and 5-t-butyl-2-methylstyrene; a styrene derivative that is substituted with a halogen atom, such as 2-chlorostyrene, 3-chlorostyrene, 4-chlorostyrene, 4-bromostyrene, 2-methyl-4,6-dichlorostyrene, and 2,4-dibromostyrene; vinylnaphthalene; and the like. It is preferable to use styrene as the aromatic vinyl monomer.

These aromatic vinyl monomers may be used either alone or in combination when producing each aromatic vinyl polymer block.

An identical aromatic vinyl monomer may be used to produce each aromatic vinyl polymer block, or a different aromatic vinyl monomer may be used to produce each aromatic vinyl polymer block.

Each aromatic vinyl polymer block ($Ar1^a$, $Ar2^a$, $Ar1^b$, and $Ar2^b$) included in the block copolymer A and the block copolymer B may include a monomer unit other than the aromatic vinyl monomer unit.

Examples of a monomer that is used to produce the monomer unit other than the aromatic vinyl monomer unit include a conjugated diene monomer such as 1,3-butadiene and isoprene (2-methyl-1,3-butadiene); an α,β-unsaturated nitrile monomer; an unsaturated carboxylic acid or acid anhydride monomer; an unsaturated carboxylic ester monomer; a non-conjugated diene monomer; and the like.

The content of the monomer unit other than the aromatic vinyl monomer unit in each aromatic vinyl polymer block is preferably 20 wt % or less, more preferably 10 wt % or less, and particularly preferably substantially 0 wt %, based on the entire aromatic vinyl polymer block.

Each conjugated diene polymer block ($D^a$ and $D^b$) included in the block copolymer A and the block copolymer B is a polymer block that includes a conjugated diene monomer unit.

A conjugated diene monomer that is used to produce the conjugated diene monomer unit is not particularly limited as long as the conjugated diene monomer is a conjugated diene compound. Examples of the conjugated diene monomer include 1,3-butadiene, isoprene, 2,3-dimethyl-1,3-butadiene, 2-chloro-1,3-butadiene, 1,3-pentadiene, 1,3-hexadiene, and the like. It is preferable to use either or both of 1,3-butadiene and isoprene as the conjugated diene monomer. It is particularly preferable to use isoprene as the conjugated diene monomer.

When the conjugated diene polymer block includes an isoprene unit, a block copolymer composition that exhibits excellent flexibility and lower tension set can be obtained.

These conjugated diene monomers may be used either alone or in combination when producing each conjugated diene polymer block. An identical conjugated diene monomer may be used to produce each conjugated diene polymer block, or a different conjugated diene monomer may be used to produce each conjugated diene polymer block. Some of the unsaturated bonds included in each conjugated diene polymer block may be hydrogenated.

Each conjugated diene polymer block ($D^a$ and $D^b$) included in the block copolymer A and the block copolymer B may include a monomer unit other than the conjugated diene monomer unit.

Examples of a monomer that is used to produce the monomer unit other than the conjugated diene monomer unit include an aromatic vinyl monomer such as styrene and α-methylstyrene; an α,β-unsaturated nitrile monomer; an unsaturated carboxylic acid or acid anhydride monomer; an unsaturated carboxylic ester monomer; a non-conjugated diene monomer; and the like.

The content of the monomer unit other than the conjugated diene monomer unit in each conjugated diene polymer block is preferably 20 wt % or less, more preferably 10 wt % or less, and particularly preferably substantially 0 wt %, based on the entire conjugated diene polymer block.

The block copolymer A included in the block copolymer composition is an asymmetric aromatic vinyl-conjugated diene-aromatic vinyl block copolymer in which an aromatic vinyl polymer block ($Ar1^a$) having a relatively low weight average molecular weight, a conjugated diene polymer block ($D^a$) having a vinyl bond content within a specific range and a weight average molecular weight within a specific range, and an aromatic vinyl polymer block ($Ar2^a$) having a relatively high weight average molecular weight, are sequentially linked to each other (see the formula (A)).

The weight average molecular weight ($Mw(Ar1^a)$) of the aromatic vinyl polymer block ($Ar1^a$) having a relatively low weight average molecular weight is 6,000 to 18,000, preferably 6,500 to 17,000, and more preferably 7,000 to 16,000.

If the weight average molecular weight $Mw(Ar1^a)$ falls outside the above range, the tension set of the resulting composition may increase to a large extent.

The weight average molecular weight ($Mw(Ar2^a)$) of the aromatic vinyl polymer block ($Ar2^a$) having a relatively high weight average molecular weight is 40,000 to 400,000, preferably 42,000 to 370,000, and more preferably 45,000 to 350,000. If the weight average molecular weight $Mw(Ar2^a)$ is too low, the tension set of the resulting composition may increase to a large extent. If the weight average molecular weight $Mw(Ar2^a)$ is too high, it may be difficult to produce the block copolymer A.

Note that the term "weight average molecular weight" used herein in connection with the polymer and the polymer block refers to a polystyrene-equivalent weight average molecular weight determined by high-performance liquid chromatography.

The ratio ($Mw(Ar2^a)/Mw(Ar1^a)$) of the weight average molecular weight ($Mw(Ar2^a)$) of the aromatic vinyl polymer block ($Ar2^a$) having a relatively high weight average molecular weight to the weight average molecular weight ($Mw(Ar1^a)$) of the aromatic vinyl polymer block ($Ar1^a$) having a relatively low weight average molecular weight is not particularly limited, but is normally 2.2 to 67, preferably 2.6 to 67, more preferably 4 to 40, and particularly preferably 4.5 to 35.

When the block copolymer A has the above configuration, it is possible to obtain a block copolymer composition that exhibits lower tension set, has a higher modulus of elasticity, and exhibits excellent elasticity.

The vinyl bond content (i.e., the ratio of a 1,2-vinyl bond and a 3,4-vinyl bond with respect to the total conjugated diene monomer units) in the conjugated diene polymer block ($D^a$) included in the block copolymer A is 1 to 20 mol %, preferably 2 to 15 mol %, and more preferably 3 to 10 mol %. If the vinyl bond content is too high, the tension set of the resulting composition may increase to a large extent.

The weight average molecular weight ($Mw(D^a)$) of the conjugated diene polymer block ($D^a$) included in the block copolymer A is 40,000 to 400,000, preferably 45,000 to 300,000, and more preferably 50,000 to 200,000.

When the weight average molecular weight ($Mw(D^a)$) of the conjugated diene polymer block ($D^a$) is within the above range, it is possible to obtain a block copolymer composition that exhibits lower tension set, has a higher modulus of elasticity, and exhibits excellent elasticity.

The content of the aromatic vinyl monomer unit in the block copolymer A based on the total monomer units included in the block copolymer A is not particularly limited, but is normally 35 to 90 wt %, preferably 40 to 87 wt %, and more preferably 43 to 85 wt %.

The weight average molecular weight of the entire block copolymer A is not particularly limited, but is normally 86,000 to 818,000, preferably 93,500 to 704,000, and more preferably 102,000 to 566,000.

The block copolymer B included in the block copolymer composition is an aromatic vinyl-conjugated diene-aromatic vinyl block copolymer in which two aromatic vinyl polymer blocks ($Ar1^b$ and $Ar2^b$) having a weight average molecular weight within a specific range are bonded to either terminal of a conjugated diene polymer block ($D^b$) having a vinyl bond content within a specific range and a weight average molecular weight within a specific range (see the formula (B)).

The weight average molecular weight ($Mw(Ar1^b)$ and $Mw(Ar2^b)$) of each aromatic vinyl polymer block ($Ar1^b$ and $Ar2^b$) included in the block copolymer B is 6,000 to 18,000, preferably 6,500 to 17,000, and more preferably 7,000 to 16,000.

If the weight average molecular weights $Mw(Ar1^b)$ and $Mw(Ar2^b)$ fall outside the above range, the tension set of the resulting composition may increase to a large extent. The weight average molecular weights ($Mw(Ar1^b)$ and $Mw(Ar2^b)$) of the two aromatic vinyl polymer blocks may be identical to each other, or may be different from each other, as long as the weight average molecular weights ($Mw(Ar1^b)$ and $Mw(Ar2^b)$) of the two aromatic vinyl polymer blocks are within the above range. It is preferable that the weight average molecular weights ($Mw(Ar1^b)$ and $Mw(Ar2^b)$) of the two aromatic vinyl polymer blocks be substantially identical to each other.

It is more preferable that the weight average molecular weight ($Mw(Ar1^b)$ or $Mw(Ar2^b)$) of at least one of the two aromatic vinyl polymer blocks be substantially identical to the weight average molecular weight ($Mw(Ar1^a)$) of the aromatic vinyl polymer block ($Ar1^a$) having a relatively low weight average molecular weight that is included in the block copolymer A.

The vinyl bond content (i.e., the ratio of a 1,2-vinyl bond and a 3,4-vinyl bond with respect to the conjugated diene monomer units in total) in the conjugated diene polymer block ($D^b$) included in the block copolymer B is 1 to 20 mol %, preferably 2 to 15 mol %, and more preferably 3 to 10 mol %.

If the vinyl bond content is too high, the tension set of the resulting composition may increase to a large extent.

It is preferable that the vinyl bond content in the conjugated diene polymer block ($D^b$) included in the block copolymer B be substantially identical to the vinyl bond content in the conjugated diene polymer block ($D^a$) included in the block copolymer A.

The weight average molecular weight (Mw($D^b$)) of the conjugated diene polymer block ($D^b$) included in the block copolymer B is 40,000 to 400,000, preferably 45,000 to 300,000, and more preferably 50,000 to 200,000.

When the weight average molecular weight (Mw($D^b$)) of the conjugated diene polymer block ($D^b$) is within the above range, it is possible to obtain a block copolymer composition that exhibits lower tension set, has a higher modulus of elasticity, and exhibits excellent elasticity.

The content of the aromatic vinyl monomer unit in the block copolymer B based on the total monomer units included in the block copolymer B is not particularly limited, but is normally 10 to 35 wt %, preferably 12 to 32 wt %, and more preferably 15 to 30 wt %.

The weight average molecular weight of the entire block copolymer B is not particularly limited, but is normally 52,000 to 436,000, preferably 58,000 to 334,000, and more preferably 64,000 to 232,000.

The molecular weight distribution (i.e., the ratio ((Mw)/(Mn)) of the weight average molecular weight (Mw) to the number average molecular weight (Mn)) of each of the block copolymer A and the block copolymer B included in the block copolymer composition according to one embodiment of the invention, and each polymer block included in the block copolymer A and the block copolymer B is not particularly limited, but is normally 1.1 or less, and preferably 1.05 or less.

The weight ratio (A/B) of the block copolymer A to the block copolymer B in the block copolymer composition according to one embodiment of the invention is 36/64 to 85/15, preferably 38/62 to 80/20, and more preferably 39/61 to 75/25.

When the block copolymer composition includes the block copolymer A and the block copolymer B in a ratio within the above range, the block copolymer composition has a high modulus of elasticity, and exhibits low tension set. If the weight ratio (A/B) of the block copolymer A to the block copolymer B is too small, the block copolymer composition may have an insufficient modulus of elasticity. If the weight ratio (A/B) of the block copolymer A to the block copolymer B is too large, the tension set of the block copolymer composition may increase to a large extent.

The block copolymer composition according to one embodiment of the invention may include only the block copolymer A and the block copolymer B as the polymer component. Note that the block copolymer composition according to one embodiment of the invention may include a polymer component other than the block copolymer A and the block copolymer B as long as the block copolymer composition falls within the scope of the invention.

Examples of the polymer component other than the block copolymer A and the block copolymer B that may be included in the block copolymer composition according to one embodiment of the invention, include an aromatic vinyl-conjugated diene-aromatic vinyl block copolymer other than the block copolymer A and the block copolymer B, an aromatic vinyl-conjugated diene block copolymer, an aromatic vinyl homopolymer, a conjugated diene homopolymer, an aromatic vinyl-conjugated diene random copolymer, and branched polymers thereof; a thermoplastic elastomer such as a polyurethane-based thermoplastic elastomer, polyamide-based thermoplastic elastomer, and a polyester-based thermoplastic elastomer; a thermoplastic resin such as polyethylene, polypropylene, polyvinyl chloride, an acrylonitrile-styrene copolymer, an acrylonitrile-butadiene-styrene copolymer, and polyphenylene ether; and the like.

The content of the polymer component other than the block copolymer A and the block copolymer B in the block copolymer composition according to one embodiment of the invention is preferably 20 wt % or less, and more preferably 10 wt % or less.

The ratio of the aromatic vinyl monomer unit to the total polymer component (i.e., the total monomer units included in the polymer component) in the block copolymer composition according to one embodiment of the invention (hereinafter may be referred to as "total aromatic vinyl monomer unit content") is 27 to 70 wt %, preferably 30 to 60 wt %, and more preferably 32 to 50 wt %.

If the total aromatic vinyl monomer unit content is too low, the resulting block copolymer composition may have an insufficient modulus of elasticity. If the total aromatic vinyl monomer unit content is too high, the tension set of the resulting block copolymer composition may increase to a large extent.

The total aromatic vinyl monomer unit content can be easily adjusted by adjusting the amounts of the block copolymer A, the block copolymer B, and the polymer component other than the block copolymer A and the block copolymer B used to produce the block copolymer composition taking account of the aromatic vinyl monomer unit content in the block copolymer A, the block copolymer B, and the polymer component other than the block copolymer A and the block copolymer B.

When the polymer component included in the block copolymer composition includes only the aromatic vinyl monomer unit and the conjugated diene monomer unit, the conjugated diene monomer unit can be decomposed, and only the aromatic vinyl monomer unit can be extracted by subjecting the polymer component included in the block copolymer composition to ozonolysis, and effecting reduction using lithium aluminum hydride according to the method described in Rubber Chem. Technol., 45, 1295 (1972). Therefore, it is possible to easily determine the total aromatic vinyl monomer unit content.

The weight average molecular weight of the entire polymer component included in the block copolymer composition according to one embodiment of the invention is not particularly limited, but is normally 60,000 to 700,000, preferably 80,000 to 600,000, and more preferably 100,000 to 500,000.

The molecular weight distribution (i.e., the ratio ((Mw)/(Mn)) of the weight average molecular weight (Mw) to the number average molecular weight (Mn)) of the entire polymer component included in the block copolymer composition according to one embodiment of the invention is not particularly limited, but is normally 1.01 to 10, preferably 1.02 to 5, and more preferably 1.03 to 3.

The block copolymer composition according to one embodiment of the invention has a water content of 200 ppm by weight or less (preferably 150 ppm by weight or less) when the block copolymer composition has been formed in the shape of pellets, dried, and allowed to stand at a temperature of 37° C. and a relative humidity of 70% for 24 hours.

When the hygroscopicity of the block copolymer composition is reduced to such a level, a hole is rarely formed in a film obtained by melt-forming the block copolymer composition.

When measuring the water content in the block copolymer composition when the block copolymer composition has been formed in the shape of pellets, dried, and allowed to stand at a temperature of 37° C. and a relative humidity of 70% for 24 hours, the pellets are formed to have a cylindrical shape having an average diameter of 5 mm and an average length of about 5 mm, and the water content is measured using a Karl Fischer moisture meter.

A block copolymer composition having such a low hygroscopicity can be obtained by producing the block copolymer composition so that the block copolymer composition does not include a hygroscopic component as impurities. A specific example of this method is described later.

The block copolymer composition according to one embodiment of the invention may include a component other than the polymer component. For example, an additive such as an antioxidant, a softener, a tackifier, an antimicrobial agent, a light stabilizer, a UV absorber, a dye, a lubricant, a cross-linking agent, and a cross-linking accelerator may optionally be added to the block copolymer composition according to one embodiment of the invention.

The antioxidant that may be included in the block copolymer composition is not particularly limited. Examples of the antioxidant include a hindered phenol compound such as pentaerythritol tetrakis[3-(3,5-di-t-butyl-4-hydroxyphenyl) propionate], 2,6-di-t-butyl-p-cresol, and di-t-butyl-4-methylphenol; a thiodicarboxylate ester such as dilauryl thiopropionate; a phosphite such as tris(nonylphenyl) phosphite; and the like.

The antioxidant may be used in an arbitrary amount. The antioxidant is normally used in a ratio of 10 parts by weight or less, and preferably 0.5 to 5 parts by weight, based on 100 parts by weight of the block copolymer composition. Note that these antioxidants may be used either alone or in combination.

The block copolymer composition according to one embodiment of the invention may be produced using an arbitrary method. For example, the block copolymer composition according to one embodiment of the invention may be produced by separately producing the block copolymer A and the block copolymer B according to a known block copolymer production method, optionally adding an additional polymer component and an additive, and mixing the components using a kneading method, a solution mixing method, or the like.

Note that it is preferable to use a method for producing a block copolymer composition according to one embodiment of the invention described below so that a block copolymer composition that has a water content of 200 ppm by weight or less when the block copolymer composition has been formed in the shape of pellets, dried, and allowed to stand at a temperature of 37° C. and a relative humidity of 70% for 24 hours, can be obtained with higher productivity.

Specifically, the method for producing a block copolymer composition according to one embodiment of the invention includes:

a step (1) that polymerizes an aromatic vinyl monomer in a solvent using a polymerization initiator to obtain a solution including an aromatic vinyl polymer having an active terminal;

a step (2) that adds a conjugated diene monomer to the solution including the aromatic vinyl polymer having an active terminal that has been obtained by the step (1), and polymerizes the conjugated diene monomer to obtain a solution including an aromatic vinyl-conjugated diene block copolymer having an active terminal;

a step (3) that adds an aromatic vinyl monomer to the solution including the aromatic vinyl-conjugated diene block copolymer having an active terminal that has been obtained by the step (2), and polymerizes the aromatic vinyl monomer to obtain a solution including an aromatic vinyl-conjugated diene-aromatic vinyl block copolymer having an active terminal;

a step (4) that adds a polymerization terminator to the solution including the aromatic vinyl-conjugated diene-aromatic vinyl block copolymer having an active terminal that has been obtained by the step (3) in a ratio of less than 1 molar equivalent with respect to the active terminal to partly inactivate the active terminal of the aromatic vinyl-conjugated diene-aromatic vinyl block copolymer to obtain a solution including the block copolymer B;

a step (5) that adds an aromatic vinyl monomer to the solution including the block copolymer B that has been obtained by the step (4), and polymerizes the aromatic vinyl monomer to obtain a solution including the block copolymer B and the block copolymer A; and a step (6) that collects the block copolymer composition from the solution including the block copolymer B and the block copolymer A that has been obtained by the step (5).

Step (1)

In the step (1) included in the method for producing a block copolymer composition according to one embodiment of the invention, an aromatic vinyl monomer is polymerized in a solvent using a polymerization initiator to obtain a solution including an aromatic vinyl polymer having an active terminal.

A polymerization initiator that is generally known to have anionic polymerization activity with respect to an aromatic vinyl monomer and a conjugated diene monomer may be used as the polymerization initiator. Examples of such a polymerization initiator include an organic alkali metal compound, an organic alkaline-earth metal compound, an organic lanthanoide series rare-earth metal compound, and the like.

An organolithium compound that includes one or more lithium atoms in the molecule is particularly suitably used as the organic alkali metal compound. Specific examples of the organolithium compound include an organic monolithium compound such as ethyllithium, n-propyllithium, isopropyllithium, n-butyllithium, sec-butyllithium, t-butyllithium, hexyllithium, phenyllithium, stilbenelithium, a dialkylaminolithium, diphenylaminolithium, and ditrimethylsilylaminolithium; an organic dilithium compound such as methylenedilithium, tetramethylenedilithium, hexamethylenedilithium, isoprenyldilithium, and 1,4-dilithioethylcyclohexane; an organic trilithium compound such as 1,3,5-trilithiobenzene; and the like. Among these, an organic monolithium compound is particularly preferably used.

Examples of the organic alkaline-earth metal compound include n-butylmagnesium bromide, n-hexylmagnesium bromide, ethoxycalcium, calcium stearate, t-butoxystrontium, ethoxybarium, isopropoxybarium, ethylmercaptobarium, t-butoxybarium, phenoxybarium, diethylaminobarium, barium stearate, ethylbarium, and the like.

Specific examples of a further polymerization initiator include a polymerization initiator that forms a homogeneous system in an organic solvent and exhibits living polymerization properties, such as a composite catalyst that includes a lanthanoide series rare-earth metal compound including neodymium, samarium, gadolinium, or the like, an alkylaluminum, an alkylaluminum halide, and an alkylaluminum hydride, and a metallocene catalyst that includes titanium, vanadium, samarium, gadolinium, or the like.

Note that these polymerization initiators may be used either alone or in combination.

The polymerization initiator may be used in an arbitrary amount taking account of the molecular weight of each block copolymer. The polymerization initiator is normally used in an amount of 0.01 to 20 mmol, preferably 0.05 to 15 mmol, and more preferably 0.1 to 10 mmol, per 100 g of the monomer in total.

The solvent used for polymerization is not particularly limited as long as the solvent is inert to the polymerization initiator. For example, a linear hydrocarbon solvent, a cyclic hydrocarbon solvent, or a mixture (mixed solvent) thereof is used as the solvent.

Examples of the linear hydrocarbon solvent include a linear alkane having 4 to 6 carbon atoms and a linear alkene having 4 to 6 carbon atoms, such as n-butane, isobutane, 1-butene, isobutylene, trans-2-butene, cis-2-butene, 1-pentene, trans-2-pentene, cis-2-pentene, n-pentane, isopentane, neo-pentane, and n-hexane. Examples of the cyclic hydrocarbon solvent include an aromatic compound such as benzene, toluene, and xylene; and an alicyclic hydrocarbon compound such as cyclopentane and cyclohexane. These solvents may be used either alone or in combination.

The solvent may be used in an arbitrary amount when effecting polymerization. The solvent is normally used in such an amount that the total concentration of the block copolymers in the solution obtained by the polymerization reaction is 5 to 60 wt %, preferably 10 to 55 wt %, and more preferably 20 to 50 wt %.

A Lewis base compound may be added to a reactor used for polymerization in order to control the structure of each polymer block included in each block copolymer that is used to prepare the block copolymer composition.

Examples of the Lewis base compound include an ether such as tetrahydrofuran, diethyl ether, dioxane, ethylene glycol dimethyl ether, ethylene glycol dibutyl ether, diethylene glycol dimethyl ether, and diethylene glycol dibutyl ether; a tertiary amine such as tetramethylethylenediamine, trimethylamine, triethylamine, pyridine, and quinuclidine; an alkali metal alkoxide such as potassium t-amyloxide and potassium t-butyloxide; a phosphine such as triphenylphosphine; and the like.

The Lewis base compounds may be used either alone or in combination. The Lewis base compound is appropriately selected so that the object of the invention is not impaired.

The Lewis base compound may be added at an arbitrary timing when effecting the polymerization reaction. The timing at which the Lewis base compound is added may be appropriately determined taking account of the desired structure of each block copolymer. For example, the Lewis base compound may be added in advance before effecting (initiating) polymerization, or may be added after polymerizing some of the polymer blocks, or may be added in advance before effecting (initiating) polymerization, and further added after polymerizing some of the polymer blocks.

The polymerization reaction temperature is normally set to 10 to 150° C., preferably 30 to 130° C., and more preferably 40 to 90° C.

The time required for polymerization differs depending on the conditions, but is normally 48 hours or less, and preferably 0.5 to 10 hours.

The polymerization pressure is not particularly limited as long as the polymerization pressure is set to be within a pressure range sufficient to maintain the monomer and the solvent in a liquid phase at the polymerization temperature.

A solution including an aromatic vinyl polymer having an active terminal can be obtained by polymerizing the aromatic vinyl monomer in the solvent using the polymerization initiator under the above conditions.

The aromatic vinyl polymer having an active terminal forms the aromatic vinyl polymer block (Ar1$^a$) having a relatively low weight average molecular weight that is included in the block copolymer A that is included in the block copolymer composition, and one of the aromatic vinyl polymer blocks (Ar1$^b$ and Ar2$^b$) that are included in the block copolymer B that is included in the block copolymer composition.

Therefore, the aromatic vinyl monomer is used in an appropriate amount taking account of the desired weight average molecular weight of each polymer block.

Step (2)

In the step (2), a conjugated diene monomer is added to the solution including the aromatic vinyl polymer having an active terminal, and polymerized to obtain a solution including an aromatic vinyl-conjugated diene block copolymer having an active terminal. When the conjugated diene monomer is added and polymerized, a conjugated diene polymer chain is formed from the active terminal to obtain a solution including an aromatic vinyl-conjugated diene block copolymer having an active terminal. The conjugated diene monomer is used in an appropriate amount taking account of the weight average molecular weight of each conjugated diene polymer block (D$^a$ and D$^b$) included in the block copolymer A and the block copolymer B.

Step (3)

In the step (3), an aromatic vinyl monomer is added to the solution including the aromatic vinyl-conjugated diene block copolymer having an active terminal, and polymerized to obtain a solution including an aromatic vinyl-conjugated diene-aromatic vinyl block copolymer having an active terminal. When the aromatic vinyl monomer is added and polymerized, an aromatic vinyl polymer chain is formed from the active terminal to obtain a solution including an aromatic vinyl-conjugated diene-aromatic vinyl block copolymer having an active terminal. The aromatic vinyl monomer is used in such an amount that the resulting aromatic vinyl polymer chain forms the other (Ar1$^b$ or Ar2$^b$) of the aromatic vinyl polymer blocks included in the desired block copolymer B. Therefore, the aromatic vinyl monomer is used in an appropriate amount taking account of the desired weight average molecular weight of the polymer block.

Step (4)

In the step (4), a polymerization terminator is added to the solution including the aromatic vinyl-conjugated diene-aromatic vinyl block copolymer having an active terminal in a ratio of less than 1 molar equivalent with respect to the active terminal to partly inactivate the active terminal of the aromatic vinyl-conjugated diene-aromatic vinyl block copolymer to obtain a solution including the block copolymer B. The aromatic vinyl-conjugated diene-aromatic vinyl block copolymer having the inactivated terminal corresponds to the block copolymer B that is included in the block copolymer composition.

The polymerization terminator that is added to the above solution is not particularly limited as long as the polymerization terminator can react with one active terminal to inactivate the active terminal, and does not react with another active terminal. A compound that does not include a halogen atom is preferable as the polymerization terminator from the viewpoint of obtaining a block copolymer composition having low hygroscopicity. It is particularly preferable to use a polymerization terminator that produces a metal alkoxide, a metal aryloxide, or a metal hydroxide through the reaction with the active terminal. Examples of a compound that is particularly preferably used as the polymerization terminator include water, a monohydric alcohol such as methanol and ethanol, and a monohydric phenol such as phenol and cresol.

The polymerization terminator is added in an appropriate amount taking account of the ratio of the block copolymer A to the block copolymer B in the block copolymer composition. The polymerization terminator may be added in an arbitrary amount as long as the polymerization terminator is added in a ratio of less than 1 molar equivalent with respect to the active terminal of the polymer. The polymerization terminator is normally added in a ratio of 0.18 to 0.91 molar equivalents, and preferably 0.35 to 0.80 molar equivalents, with respect to the active terminal of the polymer.

When the polymerization terminator is added to the solution including the aromatic vinyl-conjugated diene-aromatic vinyl block copolymer having an active terminal in a ratio of less than 1 molar equivalent with respect to the active terminal, the active terminal of the aromatic vinyl-conjugated diene-aromatic vinyl block copolymer is partly inactivated, and the polymer having the inactivated terminal corresponds to the block copolymer B that is included in the block copolymer composition. The aromatic vinyl-conjugated diene-aromatic vinyl block copolymer having an active terminal that has not reacted with the polymerization terminator remains in the solution in an unreacted state.

Step (5)

In the step (5), an aromatic vinyl monomer is added to the solution obtained as described above, and polymerized to obtain a solution including the block copolymer A and the block copolymer B.

When the aromatic vinyl monomer is added to the solution obtained by the step (4), the aromatic vinyl monomer is polymerized from (with) the aromatic vinyl polymer chain (having an active terminal) of the aromatic vinyl-conjugated diene-aromatic vinyl block copolymer having an active terminal that has not reacted with the polymerization terminator so that the aromatic vinyl polymer chain is extended. The resulting aromatic vinyl-conjugated diene-aromatic vinyl block copolymer corresponds to the block copolymer A that is included in the block copolymer composition.

The aromatic vinyl polymer chain thus extended corresponds to the aromatic vinyl polymer block ($Ar2^a$) having a relatively high weight average molecular weight that is included in the block copolymer A included in the block copolymer composition.

Therefore, the aromatic vinyl monomer is used in an appropriate amount taking account of the weight average molecular weight of the aromatic vinyl polymer block that has not been extended, and the desired weight average molecular weight of the aromatic vinyl polymer block ($Ar2^a$).

The asymmetric aromatic vinyl-conjugated diene-aromatic vinyl block copolymer that corresponds to the block copolymer A is formed by the step (5) that adds the aromatic vinyl monomer to obtain a solution including the block copolymer A and the block copolymer B.

Step (6)

In the step (6) included in the method for producing a block copolymer composition according to one embodiment of the invention, the desired block copolymer composition is collected from the solution including the block copolymer B and the block copolymer A that has been obtained as described above.

The block copolymer composition may be collected using an ordinary (arbitrary) method. For example, a polymerization terminator (see above) is optionally added to the solution including the block copolymer B and the block copolymer A after completion of the reaction to inactivate the active terminal of the polymer having an active terminal, an additive (e.g., antioxidant) is optionally added to the solution, and a known solvent removal method (e.g., direct drying method or steam stripping method) is applied to the solution to collect the desired block copolymer composition.

When the block copolymer composition is collected in the form of a slurry by applying a steam stripping method or the like, it is preferable to dehydrate the block copolymer composition using an arbitrary dehydrator (e.g., extruder-type squeezer) to collect a crumb-like block copolymer composition, and dry the crumb-like block copolymer composition using an arbitrary dryer (e.g., band dryer or expansion extruder-dryer). The block copolymer composition thus obtained may be formed in the shape of pellets or the like according to an ordinary method before use.

For example, it is preferable to use the solid (e.g., pellet-like or crumb-like) block copolymer composition after reducing the water content in the solid block copolymer composition using a dryer (e.g., hopper dryer, hot air circulation shelf-type dryer, shelf-type vacuum dryer, or stirring-type vacuum dryer).

The drying conditions are not particularly limited as long as the desired water content can be obtained, and may be set taking account of the water content to be reduced, the type of drier, and the like. The drying temperature is normally set to 40 to 90° C., and the drying time is normally set to 1 to 24 hours.

Since the method for producing a block copolymer composition according to one embodiment of the invention can successively produce the block copolymer A and the block copolymer B in an identical reaction vessel (reactor), it is possible to obtain the desired block copolymer composition with very high productivity as compared with the case where the block copolymers are separately produced, and then mixed.

The resulting block copolymer composition exhibits low hygroscopicity as compared with the block copolymer compositions specifically disclosed in Patent Literature 1 (WO2009/123089) and Patent Literature 2 (JP-A-2010-202716), and has a water content of 200 ppm by weight or less when the block copolymer composition has been formed in the shape of pellets, dried, and allowed to stand at a temperature of 37° C. and a relative humidity of 70% for 24 hours. As a result, the formation of a hole rarely occurs even when a film is formed by melt-forming the block copolymer composition after handling the block copolymer composition in air for a long time.

The reasons why the block copolymer composition obtained using the method for producing a block copolymer composition according to one embodiment of the invention exhibits low hygroscopicity are not necessarily clear. It is conjectured that, while the block copolymer compositions specifically disclosed in Patent Literature 1 (WO2009/123089) and Patent Literature 2 (JP-A-2010-202716) exhibit high hygroscopicity due to a by-product (impurities) produced when the coupling agent reacts with the active terminal, the block copolymer composition obtained using the method for producing a block copolymer composition according to one embodiment of the invention exhibits low hygroscopicity since the block copolymer composition does not include a by-product (impurities) that is produced when a coupling agent reacts with the active terminal.

The application of the block copolymer composition according to one embodiment of the invention is not particularly limited. For example, the block copolymer composition according to one embodiment of the invention may be used as a forming material that is used for an elastic film, gloves, an elastic band, a condom, office automation equipment, various rollers (used as office supplies and the like), a vibration-proof sheet used for an electric/electronic instrument, a vibration-proof rubber, an impact-absorbing sheet, an impact buffer film/sheet, a residential damping sheet, a damper material, and the like, a pressure-sensitive adhesive used for a pressure-sensitive adhesive tape, a pressure-sensitive adhesive sheet, a pressure-sensitive adhesive label, a pressure-sensitive adhesive layer for a surface protective film, a cleaning roller, and the like, an adhesive used for a sanitary article and bookbinding, an elastic fiber used for clothes and sporting goods, and the like.

Since the block copolymer composition according to one embodiment of the invention has a high modulus of elasticity, exhibits low tension set, and ensures that the formation of a hole is prevented when a film is formed by melt-forming the block copolymer composition, the block copolymer composition according to one embodiment of the invention may particularly suitably be used as a material for producing an elastic film that is used for a sanitary article such as a disposable diaper and a sanitary item.

An elastic film may be produced using the block copolymer composition according to one embodiment of the invention in an arbitrary way. A known forming method such as a melt forming method and a solvent forming method may be used without specific limitations. It is particularly preferable to use a melt forming method from the viewpoint of productivity taking account of the fact that the block copolymer composition according to one embodiment of the invention ensures that the formation of a hole is prevented when a film is formed by melt-forming the block copolymer composition.

A film according to one embodiment of the invention is obtained by melt-forming the block copolymer composition according to one embodiment of the invention. The block copolymer composition according to one embodiment of the invention may be melt-formed using various melt forming methods when producing a film. It is preferable to use an extrusion method (melt extrusion) method from the viewpoint of obtaining a smooth and flat film with high productivity. It is particularly preferable to use an extrusion method that utilizes a T-die. Specific examples of the extrusion method that utilizes a T-die include a method that extrudes the block copolymer composition melted at 150 to 250° C. from a T-die provided to a single-screw extruder or a twin-screw extruder, and winds the extruded product around a take-up roll with cooling. The film may be stretched when cooling the film using the take-up roll. A film may be formed by coating a base formed of polyethylene terephthalate, polyethylene, polypropylene, a nonwoven fabric, or a release paper with the molten block copolymer composition, or may be formed by sandwiching the molten block copolymer composition between the bases.

The resulting film may be used in a state in which the film is integrated with the base, or may be used after removing the film from the base. The thickness of the film is adjusted taking account of the application. When the film is used for a sanitary article (e.g., disposable diaper or sanitary item), the thickness of the film is normally 0.01 to 5 mm, preferably 0.03 to 1 mm, and more preferably 0.05 to 0.5 mm.

EXAMPLES

The invention is further described below by way of examples and comparative examples. Note that the units "parts" and "%" used in connection with the examples respectively refer to "parts by weight" and "wt %" unless otherwise indicated.

The measurement methods used in connection with the examples are described below.
Weight Average Molecular Weight The weight average molecular weight was determined as a polystyrene-equivalent molecular weight by high-performance liquid chromatography using tetrahydrofuran as a carrier (flow rate: 0.35 ml/min). High-performance liquid chromatography was performed using a GPC system "HLC8320" manufactured by Tosoh Corporation, and a column "Shodex (registered trademark) KF-404HQ" (×3) manufactured by Showa Denko K.K. (column temperature: 40° C.). A differential refractometer and an ultraviolet detector were used as a detector, and the molecular weight was calibrated (12 points) using standard polystyrene (molecular weight: 500 to 3,000,000) manufactured by Polymer Laboratories Ltd.
Weight Ratio of each Block Copolymer in Block Copolymer Composition The weight ratio of each block copolymer in the block copolymer composition was calculated from the area ratio of a peak (corresponding to each block copolymer) in a chart obtained by high-performance liquid chromatography (see above).
Weight Average Molecular Weight of Styrene Polymer Block Included in Block Copolymer The block copolymer was reacted with ozone, and reduced using lithium aluminum hydride according to the method described in Rubber Chem. Technol., 45, 1295 (1972) to decompose the isoprene polymer block included in the block copolymer.

Specifically, a reaction vessel charged with 100 ml of dichloromethane treated with a molecular sieve was charged with 300 mg of the sample to effect dissolution. The reaction vessel was placed in a cooling bath, and cooled to −25° C., and ozone produced using an ozonizer was introduced into the reaction vessel while passing oxygen through the reaction vessel at a flow rate of 170 ml/min. After 30 minutes had elapsed from the start of the reaction, a gas that flowed out from the reaction vessel was introduced into a potassium iodide aqueous solution to confirm completion of the reaction. Another reaction vessel in which the internal atmosphere had been replaced by nitrogen, was charged with 50 ml of diethyl ether and 470 mg of lithium aluminum hydride, and the solution reacted with ozone was slowly added dropwise to the reaction vessel while cooling the reaction vessel with ice water. The reaction vessel was placed in a water bath, and gradually increased in temperature, and the mixture was refluxed at 40° C. for 30 minutes. Dilute hydrochloric acid was added dropwise to the reaction vessel in small quantities while stirring the solution until the generation of hydrogen was hardly observed. After completion of the reaction, a solid product included in the solution was filtered off, and extracted with 100 ml of diethyl ether for 10 minutes. The extract and the filtrate were combined, and the solvent was evaporated to obtain a solid sample. The weight average molecular weight of the sample thus obtained was measured as described above, and taken as the weight average molecular weight of the styrene polymer block.

Weight Average Molecular Weight of Isoprene Polymer Block Included in Block Copolymer The weight average molecular weight of the corresponding styrene polymer block (measured as described above) was subtracted from the weight average molecular weight of the block copolymer (measured as described above), and the weight average molecular weight of the isoprene polymer block was calculated based on the resulting value.

Styrene Unit Content in Block Copolymer

The styrene unit content in the block copolymer was calculated based on the detection intensity ratio of the differential refractometer and the ultraviolet detector during high-performance liquid chromatography (see above). Note that a calibration curve was drawn in advance using copolymers differing in styrene unit content.

Styrene Unit Content in (Entire) Block Copolymer Composition

The styrene unit content in the (entire) block copolymer composition was calculated based on the proton NMR measurement results.

Vinyl Bond Content in Isoprene Polymer Block

The vinyl bond content in the isoprene polymer block was calculated based on the proton NMR measurement results.

Water Content in Block Copolymer Composition

The pellets formed of the block copolymer composition (i.e., measurement target) were dried for 1 hour in an oven adjusted to 105° C. The dried pellets were allowed to stand for 24 hours in a thermo-hygrostat adjusted to 37° C. and 70% RH (relative humidity). The pellets were then removed from the thermo-hygrostat, and the water content in the pellets (sample) was immediately measured.

The water content was measured using a Karl Fischer moisture meter ("Moisture Meter CA-200" manufactured by Mitsubishi Chemical Analytech Co., Ltd.) provided with a water vaporizer ("VA-200" manufactured by Mitsubishi Chemical Analytech Co., Ltd.) (sample heating temperature; 200° C., sample heating time: 2 minutes).

Evaluation of Formation of Hole when Film is Formed by Melt Forming

The pellets formed of the block copolymer composition (i.e., sample) were allowed to stand at room temperature (25° C.) for 7 days in air immediately after production. The pellets were then put in a single-screw extruder provided with a T-die, heated and melted at 205° C., and extruded to form a film having a thickness of 40 μm. A sample (length: 10 m) was collected from the extruded film after the forming state had become stable, and the number of holes observed in the sample was counted. It was determined that the capability to prevent the formation of a hole was better as the number of holes thus counted was smaller.

The details of the film-forming conditions employed during this evaluation were as follows.
Composition processing speed: 4.5 kg/hr
Film take-up speed: 9.5 m/min
Extruder temperature: 205° C. (inlet: 195° C., T-die: 220° C.)
Screw: full-flight screw
Extruder L/D: 32
T-die: width: 200 mm, lip: 0.5 mm Tensile Modulus of Film Two films (samples) having a width of 25 mm were cut from the measurement target film, and the tensile modulus of each film was measured so that the direction of tension coincided with the direction perpendicular to the melt flow direction during forming.

The measurement procedure is described below.

The sample was secured on a tensilon versatile tester ("RTC-1210" manufactured by ORIENTEC) in a state in which no tension was applied to the sample (chuck-to-chuck distance: 40 mm). The sample was stretched up to 200% at a rate of 300 mm/min, and then returned to the initial chuck-to-chuck distance at a rate of 300 mm/min. The sample was then stretched up to 200% at a rate of 300 mm/min, and returned to the initial chuck-to-chuck distance at a rate of 300 mm/min. The tensile stress at a stretch ratio of 50% was measured when the sample was returned to the initial chuck-to-chuck distance for the second time to calculate the tensile modulus of the elastic film at a stretch ratio of 50%. It was determined that a sample having a higher tensile modulus had a higher modulus of elasticity.

Tension Set of Film

The tension set of the film (sample) was measured using the above tensilon versatile tester in accordance with ASTM 412 so that the direction of tension coincided with the direction perpendicular to the melt flow direction during forming.

More specifically, the sample was prepared to have the Die A shape, and the benchmark distance before stretching was set to 40 mm. The film was stretched at a stretch ratio of 100%, held for 10 minutes, allowed to rapidly shrink, and allowed to stand for 10 minutes. The benchmark distance was then measured, and the tension set was calculated using the following expression.

$$\text{Tension set (\%)} = (L_1 - L_0)/(L_0 \times 100)$$

$L_0$: Benchmark distance (mm) before stretching
$L_1$: Benchmark distance (mm) after the sample was allowed to shrink, and allowed to stand for 10 minutes Example 1

(1) Production of Block Copolymer Composition

A pressure-resistant reactor was charged with 23.3 kg of cyclohexane, 1.6 mmol of N,N,N',N'-tetramethylethylenediamine (hereinafter referred to as "TMEDA"), and 0.91 kg of styrene. 104.4 mmol of n-butyllithium (1.6 M solution) was added to the mixture while stirring the mixture at 40° C. After the addition, the mixture was heated to 50° C. to effect a polymerization reaction for 1 hour. The polymerization conversion ratio of styrene was 100 wt %.

5.20 kg of isoprene was continuously added to the reactor over 1 hour while maintaining the temperature of the mixture at 50 to 60° C. After the addition, a polymerization reaction was effected for a further 1 hour. The polymerization conversion ratio of isoprene was 100%.

0.91 kg of styrene was continuously added to the reactor over 1 hour while maintaining the temperature of the mixture at 50 to 60° C. After the addition, a polymerization reaction was effected for a further 1 hour to obtain a solution including a styrene-isoprene-styrene triblock copolymer having an active terminal. The polymerization conversion ratio of styrene was 100%.

After the addition of 64.1 mmol of methanol (polymerization terminator), the mixture was mixed to partly inactivate the active terminal of the styrene-isoprene-styrene triblock copolymer to obtain a solution including a styrene-isoprene-styrene triblock copolymer (block copolymer B).

2.97 kg of styrene was then continuously added to the reactor over 1 hour while maintaining the temperature of the mixture at 50 to 60° C. After the addition, a polymerization reaction was effected for a further 1 hour to obtain a solution including a styrene-isoprene-styrene triblock copolymer having an active terminal (block copolymer A). The polymerization conversion ratio of styrene was 100%.

After the addition of 64.1 mmol of methanol (polymerization terminator), the mixture was mixed to inactivate the active terminal of the styrene-isoprene-styrene triblock copolymer to terminate the polymerization reaction.

The amount of each reagent used for the reaction is shown in Table 1. The reaction mixture including the block copolymer composition thus obtained was sampled, and the weight average molecular weight of each block copolymer included in the composition, the weight ratio of each block copolymer in the composition, the weight average molecular weight of the styrene polymer block included in each block copolymer, the weight average molecular weight of the isoprene polymer block included in each block copolymer, the styrene unit content in each block copolymer, the styrene unit content in the (entire) block copolymer composition, and the vinyl bond content in the isoprene polymer block included in each block copolymer were determined. The results are shown in Table 2.

(2) Collection of Block Copolymer Composition 0.3 parts of 2,6-di-t-butyl-p-cresol (antioxidant) was added to 100 parts of the reaction mixture obtained as described above, and the resulting mixture was mixed. The mixture (mixed solution) was added dropwise (in small quantities) to heated water (85 to 95° C.), and the solvent was volatilized to obtain a precipitate. The precipitate thus obtained was pulverized, and dried with hot air at 85° C. to collect a crumb-like block copolymer composition.

The crumb-like block copolymer composition thus collected was supplied to a single-screw extruder provided with an underwater hot cut device (provided at the end), and formed in the shape of cylindrical pellets having an average diameter of 5 mm and an average length of about 5 mm.

The pellets (formed of the block copolymer composition) were put in a hopper dryer heated at 60° C., and dried for 10 hours while circulating dry air at 60° C.

The water content in the block copolymer composition was measured, and the formation of a hole when a film was formed by melt-forming the block copolymer composition was evaluated using the dried pellets (formed of the block copolymer composition) (sample).

The results are shown in Table 2.

The pellets (formed of the block copolymer composition) dried as described above were heated and melted at 200° C., and extruded using a twin-screw extruder provided with a T-die to form a film having a thickness of 0.2 mm.

The tensile modulus and the tension set of the film were measured. The results are shown in Table 2. The details of the film-forming conditions were as follows.
Composition processing speed: 15 kg/hr
Film take-up speed: 10 m/min
Extruder temperature: inlet: 200° C., T-die: 220° C.
Screw: full-flight screw
Extruder L/D: 42
T-die: width: 300 mm, lip: 1 mm Examples 2 and 3

A block copolymer composition was produced in the same manner as in Example 1, except that the amounts of styrene, n-butyllithium, TMEDA, isoprene, and methanol were changed as shown in Table 1, and pellets and a film were prepared using the block copolymer composition.

The properties of the block copolymer composition, the pellets, and the film were measured in the same manner as in Example 1. The results are shown in Table 2.

Comparative Example 1

A pressure-resistant reactor was charged with 23.3 kg of cyclohexane, 2.6 mmol of TMEDA, and 1.80 kg of styrene. 175.7 mmol of n-butyllithium (1.6 M solution) was added to the mixture while stirring the mixture at 40° C. After the addition, the mixture was heated to 50° C., and a polymerization reaction was effected for 1 hour. The polymerization conversion ratio of styrene was 100%.

5.20 kg of isoprene was continuously added to the reactor over 1 hour while maintaining the temperature of the mixture at 50 to 60° C. After the addition, a polymerization reaction was effected for a further 1 hour. The polymerization conversion ratio of isoprene was 100%.

After the addition of 60.6 mmol of dimethyldichlorosilane, a coupling reaction was effected for 2 hours to obtain a solution including a styrene-isoprene-styrene triblock copolymer (block copolymer B).

3.00 kg of styrene was then continuously added to the reactor over 1 hour while maintaining the temperature of the mixture at 50 to 60° C. After the addition, a polymerization reaction was effected for a further 1 hour to obtain a solution including a styrene-isoprene-styrene triblock copolymer having an active terminal (block copolymer A). The polymerization conversion ratio of styrene was 100%.

After the addition of 351.4 mmol of methanol (polymerization terminator), the mixture was mixed to inactivate the active terminal of the styrene-isoprene-styrene triblock copolymer to terminate the polymerization reaction.

The amount of each reagent used for the reaction is shown in Table 1.

The properties of the block copolymer composition were measured in the same manner as in Example 1, and pellets and a film were prepared using the block copolymer composition. The properties of the pellets and the film were measured in the same manner as in Example 1.

The results are shown in Table 2.

Comparative Examples 2 and 3

A block copolymer composition was produced in the same manner as in Comparative Example 1, except that the amounts of styrene, n-butyllithium, TMEDA, isoprene, dimethyldichlorosilane, and methanol were changed as shown in Table 1, and pellets and a film were prepared using the block copolymer composition.

The properties of the block copolymer composition, the pellets, and the film were measured in the same manner as in Example 1. The results are shown in Table 2.

TABLE 1

|  | Example | | | Comparative Example | | |
| --- | --- | --- | --- | --- | --- | --- |
|  | 1 | 2 | 3 | 1 | 2 | 3 |
| Cyclohexane (kg) | 23.3 | 23.3 | 23.3 | 23.3 | 23.3 | 23.3 |
| TMEDA (mmol) | 1.6 | 1.6 | 1.4 | 2.6 | 2.3 | 2.2 |
| n-Butyllithium (mmol) | 104.4 | 104.3 | 94.9 | 175.7 | 154.7 | 147.7 |
| Styrene (kg) (first step of polymerization) | 0.91 | 1.00 | 0.89 | 1.80 | 1.55 | 1.63 |
| Isoprene (kg) (second step of polymerization) | 5.20 | 6.00 | 6.50 | 5.20 | 6.00 | 6.50 |
| Dimethyldichlorosilane (mmol) (after second step of polymerization) | — | — | — | 60.6 | 52.1 | 50.8 |
| Styrene (kg) (third step of polymerization) | 0.91 | 1.00 | 0.89 | — | — | — |
| Methanol (mmol) (after third step of polymerization) | 64.1 | 69.9 | 64.1 | — | — | — |
| Styrene (kg) (fourth step of polymerization) | 2.97 | 2.00 | 1.72 | 3.00 | 2.45 | 1.88 |
| Methanol (mmol) (after fourth step of polymerization) | 208.8 | 208.5 | 189.8 | 351.4 | 309.4 | 295.5 |

TABLE 2

|  | Example | | | Comparative Example | | |
| --- | --- | --- | --- | --- | --- | --- |
|  | 1 | 2 | 3 | 1 | 2 | 3 |
| Block copolymer A | | | | | | |
| Weight average molecular weight (Mw(Ar1$^a$)) of styrene block (Ar1$^a$) having relatively low weight average molecular weight | 10,000 | 11,000 | 10,000 | 10,400 | 10,000 | 11,000 |
| Weight average molecular weight (Mw(Ar2$^a$)) of styrene block (Ar2$^a$) having relatively high weight average molecular weight | 95,000 | 78,000 | 75,000 | 85,000 | 74,000 | 63,000 |
| Mw(Ar2$^a$)/Mw(Ar1$^a$) | 9.5 | 7.1 | 7.5 | 8.2 | 7.4 | 5.7 |
| Weight average molecular weight (Mw(D$^a$)) of isoprene block | 72,000 | 89,000 | 99,000 | 36,600 | 46,000 | 73,000 |
| Vinyl bond content (%) in isoprene block | 7 | 7 | 7 | 7 | 7 | 7 |
| Weight average molecular weight of block copolymer A | 177,000 | 178,000 | 184,000 | 132,000 | 130,000 | 147,000 |
| Styrene unit content (%) in block copolymer A | 65 | 57 | 52 | 69 | 60 | 54 |
| Block copolymer B | | | | | | |
| Weight average molecular weight (Mw(Ar1$^b$) = Mw(Ar2$^b$)) of styrene block | 10,000 | 11,000 | 10,000 | 10,400 | 10,000 | 11,000 |
| Weight average molecular weight (Mw(D$^b$)) of isoprene block | 72,000 | 89,000 | 99,000 | 99,200 | 108,000 | 132,000 |
| Vinyl bond content (%) in isoprene block | 7 | 7 | 7 | 7 | 7 | 7 |
| Weight average molecular weight of polymer B | 92,000 | 111,000 | 119,000 | 120,000 | 128,000 | 154,000 |
| Styrene unit content (%) in polymer B | 26 | 25 | 22 | 26 | 21 | 20 |
| (entire) Block copolymer composition | | | | | | |
| Weight average molecular weight | 140,500 | 140,000 | 146,000 | 125,000 | 129,000 | 151,000 |
| Molecular weight distribution | 1.08 | 1.10 | 1.07 | 1.12 | 1.03 | 1.10 |
| Styrene unit content (%) | 48 | 40 | 35 | 48 | 40 | 35 |
| Block copolymer A/block copolymer B (weight ratio) | 57/43 | 43/57 | 42/58 | 45/55 | 43/57 | 38/62 |
| Water content (ppm by weight) | 85 | 100 | 110 | 1,200 | 1,100 | 1,000 |
| Evaluation of formation of hole when film was formed by melt forming (number of holes observed) (per 10 m) | 0 | 0 | 0 | 45 | 50 | 35 |
| Performance of film | | | | | | |
| 50% tensile modulus (MPa) | 0.98 | 0.86 | 0.69 | 0.94 | 0.80 | 0.62 |
| Tension set (%) | 4 | 2 | 2 | 4 | 2 | 2 |

As is clear from the results shown in Table 2, the block copolymer compositions of Examples 1 to 3 that were produced without using dimethyldichlorosilane (coupling agent) had a water content of 200 ppm by weight or less when the block copolymer composition had been formed in the shape of pellets, dried, and allowed to stand at a temperature of 37° C. and a relative humidity of 70% for 24 hours. When a film was formed by melt-forming the block copolymer compositions of Examples 1 to 3, the formation of a hole was not observed.

On the other hand, the block copolymer compositions of Comparative Examples 1 to 3 that were produced using dimethyldichlorosilane as a coupling agent had a water content significantly higher than 200 ppm by weight when the block copolymer composition had been formed in the shape of pellets, dried, and allowed to stand at a temperature of 37° C. and a relative humidity of 70% for 24 hours. When a film was formed by melt-forming the block copolymer compositions of Comparative Examples 1 to 3, a number of holes formed in the film were observed.

It was thus confirmed that the formation of a hole can be prevented when a film is formed by melt-forming the block copolymer composition according to the embodiments of the invention that has a water content of 200 ppm by weight or less when the block copolymer composition has been formed in the shape of pellets, dried, and allowed to stand at a temperature of 37° C. and a relative humidity of 70% for 24 hours.

The invention claimed is:
1. A method for producing a block copolymer composition having a water content of 200 ppm by weight or less when the block copolymer composition has been formed in a shape of pellets, dried, and allowed to stand at a temperature of 37° C. and a relative humidity of 70% for 24 hours, the method comprising:

a step (1) that polymerizes an aromatic vinyl monomer in a solvent using a polymerization initiator to obtain a solution including an aromatic vinyl polymer having an active terminal;

a step (2) that adds a conjugated diene monomer to the solution including the aromatic vinyl polymer having an active terminal that has been obtained by the step (1), and polymerizes the conjugated diene monomer to obtain a solution including an aromatic vinyl-conjugated diene block copolymer having an active terminal;

a step (3) that adds an aromatic vinyl monomer to the solution including the aromatic vinyl-conjugated diene block copolymer having an active terminal that has been obtained by the step (2), and polymerizes the aromatic vinyl monomer to obtain a solution including an aromatic vinyl-conjugated diene-aromatic vinyl block copolymer having an active terminal;

a step (4) that adds a polymerization terminator to the solution including the aromatic vinyl-conjugated diene-aromatic vinyl block copolymer having an active terminal that has been obtained by the step (3) in a ratio of less than 1 molar equivalent with respect to the active terminal to partly inactivate the active terminal of the aromatic vinyl-conjugated diene-aromatic vinyl block copolymer to obtain a solution including a block copolymer B represented by a formula (B);

a step (5) that adds an aromatic vinyl monomer to the solution including the block copolymer B that has been obtained by the step (4), and polymerizes the aromatic vinyl monomer to obtain a solution including the block copolymer B and a block copolymer A represented by a formula (A); and a step (6) that collects the block copolymer composition from the solution including the block copolymer B and the block copolymer A that has been obtained by the step (5), $$Ar1^a\text{-}D^a\text{-}Ar2^a \quad (A)$$

$$Ar1^b\text{-}D^b\text{-}Ar2^b \quad (B)$$

where each of $Ar1^a$, $Ar1^b$, and $Ar2^b$ is independently an aromatic vinyl polymer block having a weight average molecular weight of 6,000 to 18,000, $Ar2^a$ is an aromatic vinyl polymer block having a weight average molecular weight of 40,000 to 400,000, and each of $D^a$ and $D^b$ is independently a conjugated diene polymer block having a vinyl bond content of 1 to 20 mol % and a weight average molecular weight of 40,000 to 400,000, and wherein the amount of the polymerization terminator added in the step (4) and the amount of the aromatic vinyl monomer added in the step (5) are determined so that a weight ratio (A/B) of the block copolymer A to the block copolymer B in the block copolymer composition being 36/64 to 85/15, and the amounts of the aromatic vinyl monomer used in the steps (1), (3) and (5) and the amount of the conjugated diene monomer added in the step (2) are determined so that a ratio of an aromatic vinyl monomer unit with respect to a total polymer component included in the block copolymer composition being 27 to 70 wt %.

* * * * *